(12) United States Patent
Fowler, Jr.

(10) Patent No.: US 6,468,207 B1
(45) Date of Patent: Oct. 22, 2002

(54) DEEP TISSUE SURGICAL RETRACTOR APPARATUS AND METHOD OF RETRACTING TISSUE

(75) Inventor: James M. Fowler, Jr., Houston, TX (US)

(73) Assignee: Lone Star Medical Products, Inc., Houston, TX (US)

(*) Notice: Subject to any disclaimer, the term of this patent is extended or adjusted under 35 U.S.C. 154(b) by 120 days.

(21) Appl. No.: 09/663,562

(22) Filed: Sep. 15, 2000

Related U.S. Application Data

(60) Provisional application No. 60/184,583, filed on Feb. 4, 2000.

(51) Int. Cl.[7] .................................................. A61B 1/32
(52) U.S. Cl. ...................... 600/233; 600/217; 600/219; 600/231; 600/232
(58) Field of Search .................................... 600/210, 213, 600/217, 219, 231, 232, 233

(56) References Cited

U.S. PATENT DOCUMENTS

| | | | |
|---|---|---|---|
| 1,707,689 A | * | 4/1929 | Sloan |
| 1,963,173 A | | 6/1934 | Morin |
| 2,473,266 A | * | 6/1949 | Wexler |
| 2,695,607 A | * | 11/1954 | Hipps et al. |
| 3,040,739 A | | 6/1962 | Grieshaber |
| 3,394,700 A | | 7/1968 | Yamamoto |
| 3,515,129 A | | 6/1970 | Truhan |
| 3,522,799 A | * | 8/1970 | Gauthier |
| 3,724,449 A | * | 4/1973 | Gauthier |
| 3,749,088 A | | 7/1973 | Kohlmann |
| 3,762,401 A | | 10/1973 | Tupper |
| 3,965,890 A | | 6/1976 | Gauthier |
| 4,010,741 A | | 3/1977 | Gauthier |
| 4,048,987 A | | 9/1977 | Hurson |
| 4,185,636 A | | 1/1980 | Gabbay et al. |
| 4,254,763 A | | 3/1981 | McCready et al. |
| 4,274,398 A | | 6/1981 | Scott, Jr. |
| 4,337,762 A | | 7/1982 | Gauthier |
| 4,344,420 A | | 8/1982 | Forder |
| 4,355,631 A | | 10/1982 | LeVahn |
| 4,380,999 A | | 4/1983 | Healy |
| 4,421,107 A | | 12/1983 | Estes et al. |
| 4,430,991 A | | 2/1984 | Darnell |
| 4,434,791 A | | 3/1984 | Darnell |
| RE32,021 E | | 11/1985 | Scott, Jr. |
| 4,627,421 A | * | 12/1986 | Symbas et al. |
| 5,080,088 A | | 1/1992 | LeVahn |
| 5,231,974 A | | 8/1993 | Giglio et al. |
| 5,307,805 A | | 5/1994 | Byrne |
| 5,769,783 A | | 6/1998 | Fowler |
| 5,785,649 A | | 7/1998 | Fowler, Jr. |
| 5,951,467 A | | 9/1999 | Picha et al. |
| 5,964,697 A | | 10/1999 | Fowler, Jr. |
| 5,964,698 A | | 10/1999 | Fowler |
| 6,190,312 B1 | * | 2/2001 | Fowler, Jr. .................. 600/231 |
| 6,254,532 B1 | * | 7/2001 | Paolitto et al. ............. 600/201 |

FOREIGN PATENT DOCUMENTS

| | | |
|---|---|---|
| DE | 3234875 | 3/1994 |
| GB | 1222141 | 2/1971 |
| GB | 1550254 | 8/1979 |
| GB | 1550255 | 8/1979 |

OTHER PUBLICATIONS

MD&M Review, Thermoplastic Replaces Metal in Disposable Adbominal Retractor, ULTOP® Conveyor Modules (1 page) (No Date).
*Accurate Surgical & Scientific Instruments Corporation* Brochure, Tupper's Universal Handholder and Retraction Set®, p. 39 (1 page) (No Date).

* cited by examiner

*Primary Examiner*—Jeffrey A. Smith
(74) *Attorney, Agent, or Firm*—Akin, Gump, Strauss, Hauer & Feld LLP

(57) ABSTRACT

A retractor system having a blade assembly with notches for receiving a portion of a surgical retractor stay. A retractor system having a cam lock mechanism and/or a ratchet mechanism to restrict movement of the paddle arms. A retractor system having pinions to engage an elastic band to aid the frame and paddle arms to automatically self-position during a surgical procedure.

34 Claims, 4 Drawing Sheets

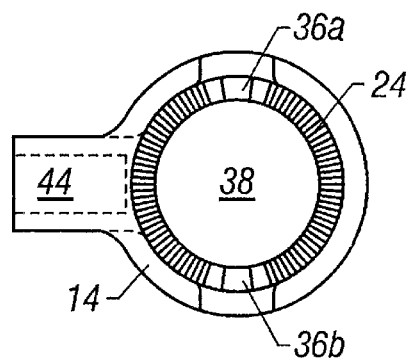
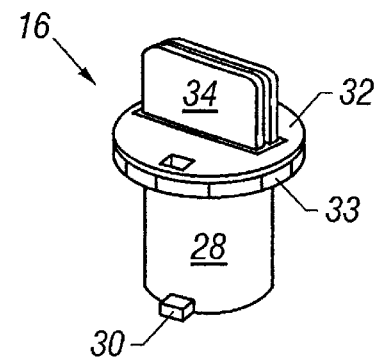
FIG. 3  FIG. 4
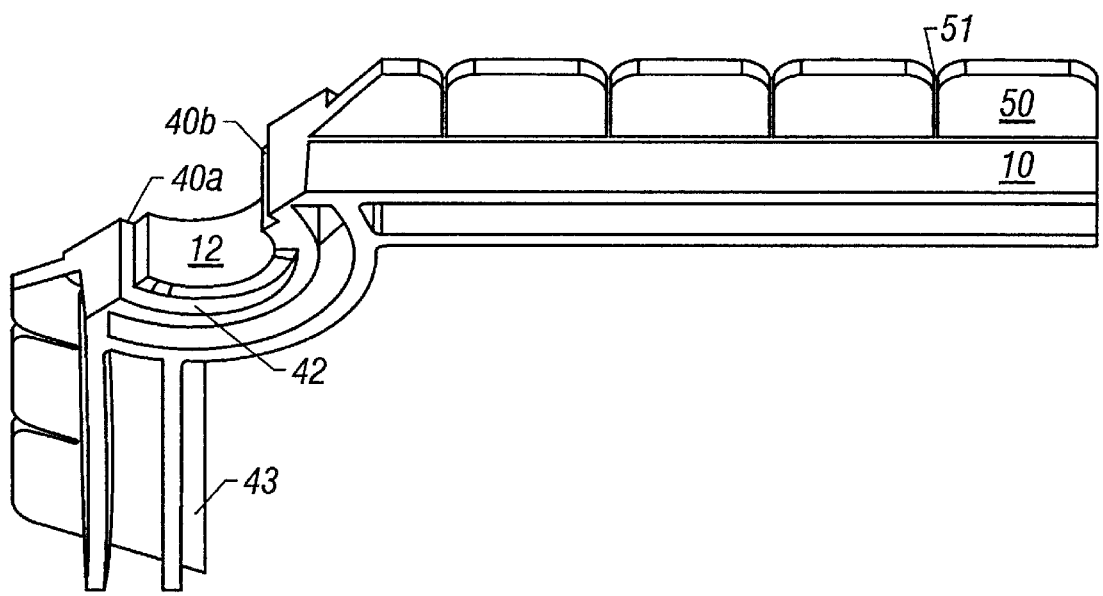
FIG. 5

DEEP TISSUE SURGICAL RETRACTOR APPARATUS AND METHOD OF RETRACTING TISSUE

CROSS-REFERENCE TO RELATED APPLICATIONS

This application claims priority to the provisional patent application Serial No. 60/184,583 filed Feb. 24, 2000.

STATEMENT REGARDING FEDERALLY SPONSORED RESEARCH

Not applicable.

BACKGROUND OF THE INVENTION

1. Field of the Invention

The present invention relates to a surgical retractor apparatus for use in surgery, particularly an apparatus including movable arms with blades to facilitate deep tissue retraction. More particularly, the present invention relates to an improved frame having a notched flange and apertures for receiving rotatable, self-positioning retractor arms and, optionally, retractor blades also having notches for use with surgical retractor stays.

2. Description of the Related Art

During the course of a surgical procedure or operation, the surgeon opens the patient with a scalpel, forming an incision and surgical site. As the surgeon cuts deeper, the operating room staff typically holds surface tissue away from the operative field using retractors. Many surgical procedures require the surgical staff to hold deep tissue and organs out of the surgical field also. Mechanical supports and/or arms are sometimes attached to the frame of the surgical table to form a stable base for deep tissue retractors.

Once an incision is separated and retracted, there is often a need for multiple stays in the form of sutures for holding various tissues, for example different organs. Retractor frames may be placed around the incision and elongated retractor stays, often having an elastic member, used to hold the incision open may be attached to the retractor frame. The elongated retractor stays may need to be repositioned during the surgical procedure which requires intervention by one of the surgical staff. Also, for some deep tissue retraction a rigid retractor arm and blade would be preferable to an elongated retractor stay. Additionally, it would be beneficial to have a retractor blade assembly capable of receiving a surgical retractor stay.

There exists a need for an improved retractor blade assembly capable of receiving a surgical retractor stay. There exists a need for an improved retractor frame that may hold both elastic retractor stays and more rigid retractor assemblies. There exists a need for an improved surgical retractor frame having arms which aid in the self-positioning of the frame during surgery. There exists a need for a deep tissue surgical retractor that does not require attaching mechanical support members to the surgical table.

SUMMARY OF THE INVENTION

The present invention provides an improved surgical retractor system that offers several benefits over the prior art. The surgical retractor system permits retraction of surface tissue and deep tissue.

One embodiment according to the present invention includes a surgical retractor system having a blade assembly with at least one notch to receive an elongated member of a surgical retractor stay. The notches may be adapted to receive elongated members of uniform diameter or elongated members having enlarged diameter sections.

One surgical retractor system according to the present invention provides a retractor frame that is self-positioning.

The present invention may also provide paddle arm hubs having teeth that cooperate with aperture projections to act as a locking ratchet mechanism. The hubs may also be adapted with a bore and optionally a hub slot to receive a locking cam pin.

One embodiment of the frame of the present invention also includes a flange having a plurality of notches for receiving surgical retractor stays.

The present invention may further provide a cam locking mechanism for use as an independent locking mechanism or as a locking mechanism in addition to the ratchet locking mechanism.

One embodiment of the present invention is a surgical retractor system for use during surgery having an articulated two-piece frame. The frame members have complimentary hinges typically coupled by pins or screws.

One embodiment of the surgical retractor system according to the present invention includes a pinion on the paddle arm hub for receiving an elastic band to aid automatic separation of the paddles as the incision is increased in size.

In another embodiment the frame and blade assembly each have notched flanges adapted to receive an elongated member of a surgical retractor stay to hold an incision open.

BRIEF DESCRIPTION OF THE DRAWINGS

For a further understanding of the nature, objects and advantages of the present invention, reference should be made to the following detailed description, read in conjunction with the following drawings, wherein like reference numerals indicate like elements and wherein:

FIG. 3 is a bottom view of the hub showing the teeth;

FIG. 4 is a perspective view of the cam lock pin;

FIG. 5 is a perspective, partial sectional view of an aperture showing the grooved indentation and ridge portion of a cam locking mechanism.

DETAILED DESCRIPTION OF INVENTION

According to the invention, the improved surgical retractor system has paddle arms and an elastic band which aid in self-positioning of the frame. The frame also includes apertures and hubs which cooperate to form a ratchet mechanism to reduce slippage of the paddle arms during a surgical procedure. A cam lock pin may engage indentations in the aperture to lock the paddle arms into a fixed position to reduce accidental movement of the arms during surgery.

Figure 1:
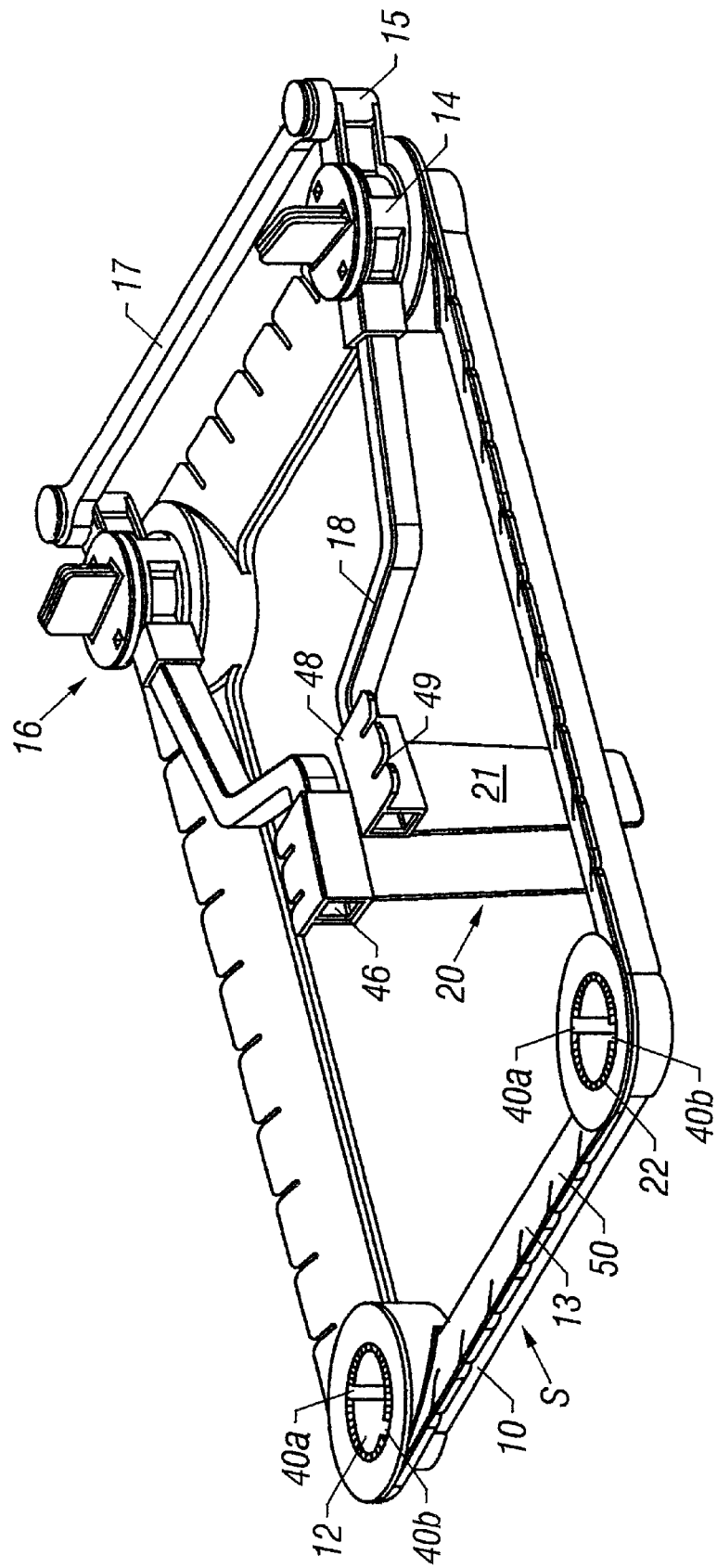
FIG. 1 is a perspective view of a one-piece frame, hubs, locking pins, arms and blades, according to a first embodiment of the surgical retractor system of the present invention.
Figure 2:
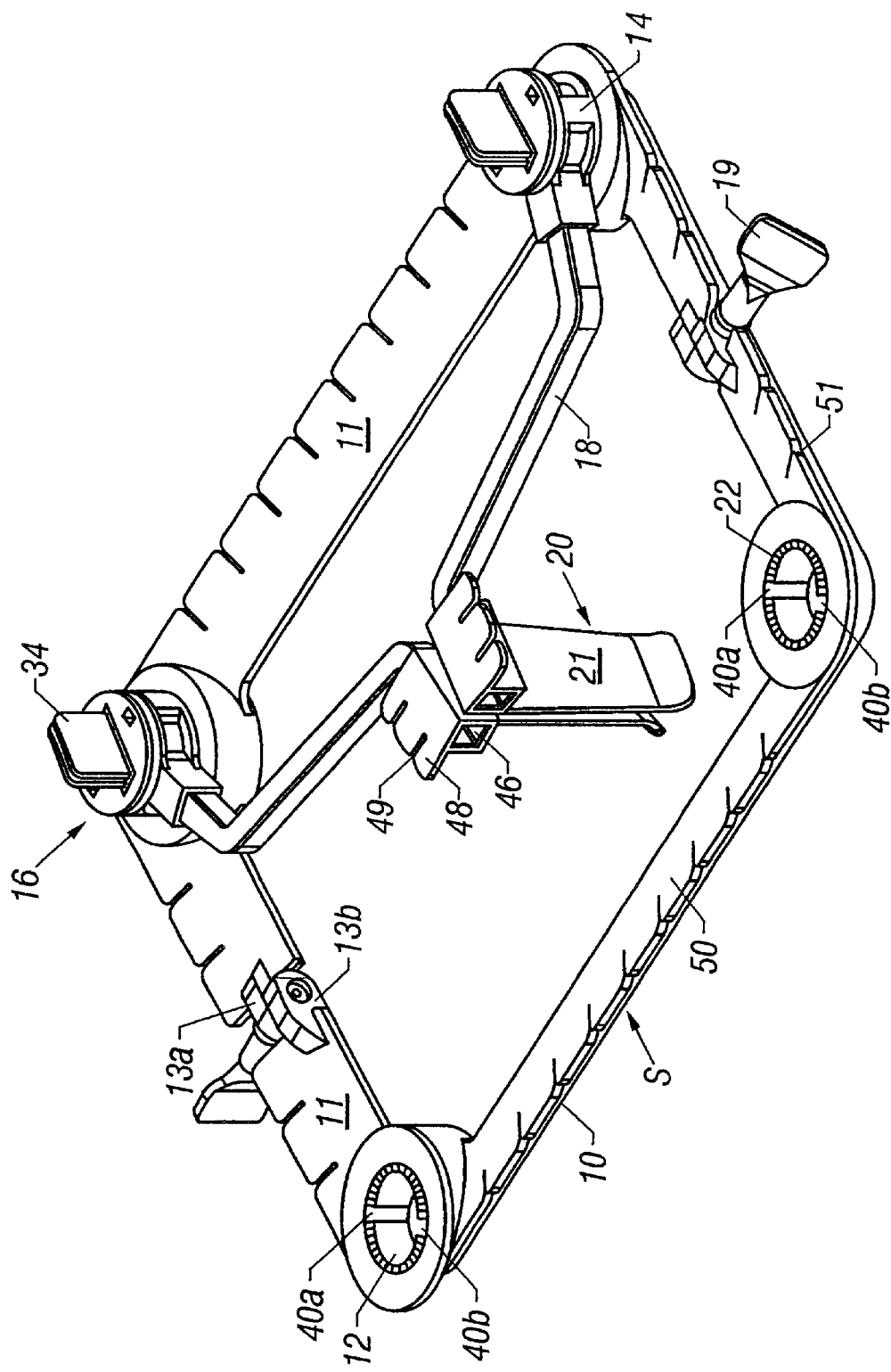
FIG. 2 is a perspective view of a two-piece frame, hubs, locking pins, arms and blades, according to an alternate embodiment of the surgical retractor system of the present invention.

The surgical retractor system of the present invention, generally referred to as S, is shown in FIGS. 1 and 2. The surgical retractor system S includes a frame 10 having a plurality of apertures 12 adapted to receive a hub 14 and a cam lock pin 16. The hub 14 is adapted to receive a paddle arm 18 having a blade assembly 20.

Figure 6:
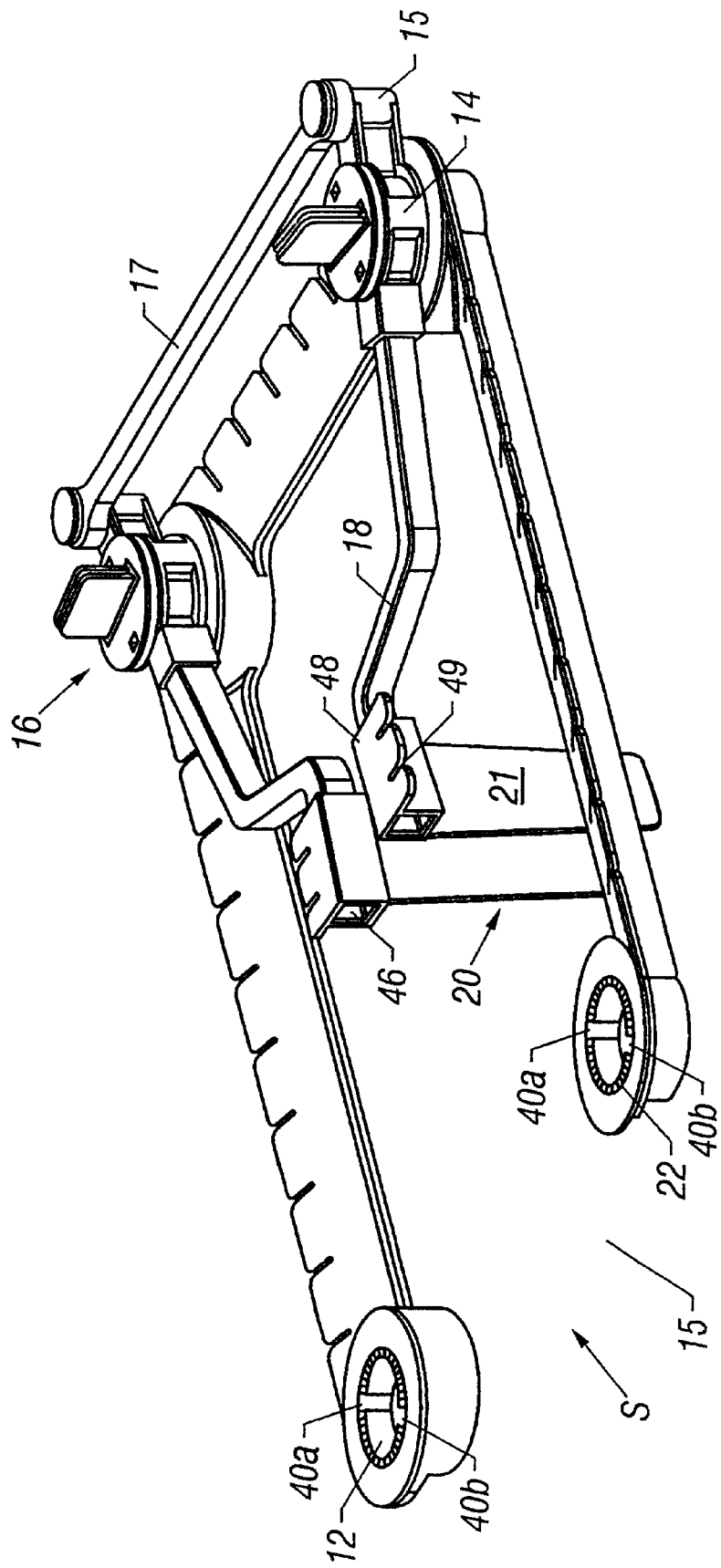
FIG. 6 is a perspective view of an open frame having an opening to improve access to the surgical site from an open side of the frame, according to another embodiment of the surgical retractor system of the present invention.

Referring to FIGS. 1 and 2, the frame 10 is generally annular and may form a closed frame to fit around a surgical incision. Alternatively, the frame 10 may be an open frame having an opening 15, as shown in FIG. 6, to improve access to the surgical site from the open side of the frame 10. The specific shape of frame 10 may be modified according to the specific surgical procedure so as to conform to the surface contour of a patient's body at the surgical site. For example, other frame configurations are disclosed in U.S. Pat. No. 4,434,791 to Darnell and U.S. Pat. No. Re. 32,201 to Scott, Jr. which are fully incorporated by reference. It is to be understood that other shape configurations are contemplated and within the scope of the present invention.

The frame 10 may have one-piece as shown in FIG. 1. Alternatively as shown in FIG. 2, frame 10 may have multiple frame members 11 to form an articulated frame which can more readily conform to the contours of the patient's body at the surgical site. The frame members 11 may have hinges 13a and 13b. The hinge 13a has a clearance hole to receive a thumb screw 19 or other coupler such as a clamping bolt. The hinge 13b has a threaded hole for receiving and retaining the thumb screw 19.

Typically, the frame 10 and frame members 11 are made of stainless steel, aluminum or other metals and may be reused after sterilization by conventional methods including, but not limited to, heat or radiation treatment. Alternatively, the frame 10 and frame members 11 may be made of inexpensive disposable materials including, but not limited to, stamped metal or molded plastic.

Alternatively, the frame 10 may have a plurality of sections of the frame comprising a relatively rigid, but flexible plastic, metal or plastic coated metal. The flexible section may be bent to allow frame 10 to better conform to the contours of the patient's body at the surgical site. The flexible section will retain its shape until force is applied to alter the shape of the frame 10 as needed during a particular surgical procedure or to prepare the shape of the frame 10 for a different surgical procedure.

The frame 10 includes a plurality of apertures 12, as shown in FIGS. 1 and 2, which are typically located in the corners of the frame 10. The apertures 12 cooperate with the hubs 14 and cam lock pin 16 to hold rotating paddle arms 18 in a selected position.

As shown in FIGS. 1 and 2, the hub 14 fits onto a plurality of teeth 22 substantially surrounding the aperture 12. As shown in FIG. 3, the bottom of hub 14 has a plurality of projections 24 which are complimentary to the teeth 22 surrounding the aperture 12. Preferably, the teeth 22 surrounding the aperture 12 and the projections 24 in the hub 14 permit the hub 14 to rotate in one direction by acting as a ratchet. This ratcheting mechanism reduces accidental rotation of the hub 14 which could reduce the tension provided by the paddle arms 18 and blades 21 leading to partial closure of the incision during the surgical procedure.

The radial movement of the hub 14 in the aperture 12, not present in prior art retractor systems, provides a method of applying radial tension to retract tissue with advantages not present in systems lacking radial movement of a hub 14 and paddle arm 18. The rotating movement of the paddle arm 18 as the hub 14 turns in the aperture 12 provides a radial tension between the paddle arm 18 and the incision or organs retracted by the blade 21. The ratcheting mechanism caused by the interaction of the teeth 22 of the aperture 12 and the projections 24 in the hub resists the radial tension exerted on the paddle arm 18 by the incision and which would tend to close the incision.

Prior art retractors have paddle blades and arms that were designed such that the paddle engages the retracted tissue or organ and creates a tension generally parallel to the length of the paddle arm. In order to increase the tension on the paddle blade in the prior art retractors the paddle arm has to be pulled generally linearly outward from the interior of the retractor frame and toward the surgeon. This linear outward motion of the paddle arm causes part of the paddle arm to extend farther outside of a frame to which the paddle arm is attached as tension on the paddle arm is increased or as the size of the incision increases. Having a portion of the paddle arm extending outside of the retractor frame increases the possibility that the paddle arm may be accidentally struck and dislodged by a member of the surgical staff. Further, when a portion of the paddle arm extends outside of the retractor frame, the extended paddle arm may limit positioning of additional equipment near the frame or may restrict access to the surgical site near the extended paddle arm.

In contrast, as shown in FIGS. 1 and 2, the radial movement of the paddle arms 18 and hubs 14 permits tension to be applied and maintained to retracted incision or organs without having to place a portion of the paddle arm 18 outside of the retractor frame 10. The present embodiments using paddle arms 18 and hubs 14 permit secure retraction using radial tension while maintaining the paddle arm 18 in the interior of the retractor frame 10 to reduce the possibility of accidentally striking the paddle arm 18. The present invention permits a more compact retractor system, i.e., the paddle arms are contained within the circumference of the retractor frame, providing more secure retraction.

One embodiment of the hub 14 includes a pinion 15, shown in FIG. 2, which is typically located approximately 180 degrees away from a channel 44, shown in FIG. 3, for receiving the paddle arm 18. The pinions 15 are adapted to receive an elastic band 17 which is typically made of silicone or other elastic medium. The elastic band 17 may be prepared to have a specific tension depending on the specific surgical procedure being performed. The elastic band 17 exerts tension on the hubs 14 which aids in the automatic opening of the incision without intervention of the surgeon when the incision increases in size. This helps to maintain retraction of deep tissue by the blades 21 and aids in the self-positioning of the surgical retractor system S.

FIG. 4 shows a cam lock pin 16 which is used in one embodiment in conjunction with the hub 14 and the frame 10 to reduce unintentional movement of the paddle arm 18 during a surgical procedure. The lock pin 16 typically includes a cylindrical body 28, one or more studs 30, a stop 32 and a handle 34. The studs 30 on the pin 16 slide through a pair of hub slots 36a and 36b as the body 28 passes through a bore 38 in the hub 14. As the lock pin 16 enters the aperture 12, the studs 30 engage grooved indentations 40a and 40b, shown in FIGS. 2 and 5. The indentations 40a and 40b transition into a pair of slanted, horizontal ridges 42. The studs 30 engage the ridges 42 as the handle 34 is rotated. As the studs 30 traverse the slanted ridges 42, pressure increases between the stop 32 and the hub 14. This increasing pressure between hub 14 and stop 32 reduces unintentional movement of hub 14. The pin 16 may be readily loosened to permit adjustment of the hub 14 and the paddle arm 18.

The pin 16 has a handle 34 that may be readily grasped to adjust the cam lock pin 16. The handle 34 may have textured surface to decrease slippage when gripping the handle 34 while wearing gloves, particularly when the gloves may be slippery due to the presence of fluids associated with the surgical procedure.

Alternatively, the pin 16 may be formed without a handle 34 to provide a pin 16 having a lower profile. The stop 32 may have a diameter greater than the diameter of the hub 14 to permit surgical staff to grip the stop 32 to adjust the pin 16 to engage the cam lock pin 16 in the ridge 42. Optionally, the stop 32 may have a textured edge 33 to reduce slippage during adjustment of the pin 16. The textured edge 33 may include, but is not limited to, grooves or ridges.

In an alternative embodiment of the present invention, the frame aperture 12 and hub 14 may be formed without the teeth 22 and projections 24, respectively. Instead, the alternative embodiment may rely upon the cam locking mechanism using the cam lock pin 16 and the grooved indentations 40a and 40b in the aperture 12. This would permit rotation of the hub 14 in either direction without having to lift the hub 14 to disengage the aperture teeth 22 and the hub projections 24. Also, the absence of the teeth 22 and projections 24 may reduce the costs of the surgical retractor system 10.

Optionally in an embodiment of the present invention, in the absence of the teeth 22 and projections 24, the hubs 14 may each have a pinion 15. The pinions 15 may be connected by an elastic band 17 which applies tension to the paddle arms 18 to automatically position the paddle arms 18 and maintain tension to retract the incision or organs. The elastic band 17 permits the elimination of a ratchet type mechanism and action to position the paddle arms 18 and retract tissue and organs. A cam lock mechanism having the cam lock pin 16 and the grooved indentations 40 and 40a in the aperture 12 may be used in conjunction with the pinions 15 and elastic band 17 to lock the hubs 14 in a desired position to reduce the possibility of slippage of the paddle arms 18 if the elastic band 17 breaks or becomes dislodged during a surgical procedure.

The hub 14 is adapted to receive a paddle arm 18, as shown in FIGS. 1 and 2. The hub 14 has a channel 44, as shown in FIG. 3, adapted to receive the paddle arm 18. The channel 44 is typically rectangular to limit the orientation of the arm 18 within the interior of the frame 10. The paddle arm 18 may be integrally formed with the paddle blade assembly 20 or the blade assembly 20 may be a separate piece having a port 46, as shown in FIGS. 1 and 2, for receiving the arm 18. Alternatively, the hub 14, arm 18 and blade assembly 20 may be integrally formed as a unitary piece. The hub 14, arm 18 and blade assembly 20 may be sterile disposable parts or may be reusable parts.

Alternatively, the paddle arm 18 may be moveably coupled to the frame 10 by any conventional method. Preferably the arm 18 is coupled to permit radial movement of the arm 18. More preferably the arm 18 is coupled such that the radial movement of the arm 18 occurs within the outer perimeter 11 of frame 10. The radial movement of the arm 18 permits the construction of a surgical retractor system have an arm 18 that is confined within the outer perimeter 11 of the frame 10 during a surgical procedure, even when the arm 18 is adjusted during the surgical procedure.

As shown in FIG. 1, the blade assembly 20 includes a blade 21 and a notched blade extension 48. The blade notches 49 are adapted to receive the elongated member of a surgical retractor stay. The blade notches 49 may be sized and shaped to receive elongated members that are uniform in diameter or that have enlarged diameter portions on the elongated member. The blade notches 49 may be adapted to receive elongated members that are elastic or relatively non-elastic metal ball and chain structures. The blade 21 is sized and shaped for the particular surgical procedure. The blade 21 may be changed during the surgical procedure when a different blade shape or size becomes appropriate. Alternatively, when the blade assembly 20, paddle arm 18 and hub 14 are a unitary piece, the entire unitary piece may be replaced with one having a blade 21 with the desired size and shape.

As shown in FIGS. 1 and 2, the frame 10 has a flange 50 having a plurality of notches 51. The flange notches 51 are sized and shaped to receive surgical retractor stays. The flange notches 51 are adapted to receive the elongated member of a surgical retractor stay. The flange notches 51 may be sized and shaped to receive elongated members that are uniform in diameter or that have enlarged diameter portions on the elongated member. The flange notches 51 may be adapted to receive elongated members that are elastic or relatively non-elastic metal ball and chain structures. The flange 50 typically has a low profile structure which may be concave to increase the accessibility of the stays for ease of placement. Also, the flange 50 may be adapted to receive a lighted surgical retractor paddle, as disclosed in Applicant's pending U.S. application Ser. No. 09/388,115 filed Sep. 1, 1999 (now abandoned) and which is fully incorporated by reference, or other attachment. The flange 50 may be adapted to allow the lighted surgical retractor paddle to snap onto the frame 10. The flange 50 cooperates with a track 43, shown in FIG. 5, to permit snap-on attachment of additional surgical equipment such as the lighted surgical retractor.

The elongated member of the surgical retractor stay may be an elastic member of uniform diameter as disclosed in U.S. Pat. Nos. 5,785,649; 5,769,783; Re. 32,021; and U.S. application Ser. No. 09/067,125, filed Apr. 27, 1999 (now U.S. Pat. No. 5,964,697), which are fully incorporated herein by reference. Alternatively, the elongated member may be a non-elastic member including, but not limited to, a ball and link member as disclosed in U.S. Pat. No. 3,762,401 which is fully incorporated herein by reference. The elongated member may have a non-uniform diameter along its length, instead having spaced apart, enlarged diameter sections such as disclosed in U.S. Pat. No. 5,785,649 which is fully incorporated by reference. Alternatively, the elongated member may be a ribbed elastic member.

The flange notches 51 are typically tapered toward the frame 10 and are generally less than the width of the elongated member to retain the retractor stay in the flange notch 51 by friction. Alternatively, the flange notches 51 may be wider than the elongated member as, for example, when the elongated member has enlarged diameter sections such as disclosed in U.S. Pat. No. 5,785,649 or when the stay has a ball and link member such as disclosed in U.S. Pat. No. 3,762,401. The enlarged diameter sections prevent the elongated members from slipping through the flange notch 51.

The blade notches 49 are typically tapered toward the port 46 and are generally less than the width of the elongated member to retain the retractor stay in the blade notch 49 by friction. Alternatively, the blade notches 49 may be wider than the elongated member as, for example, when the elongated member has enlarged diameter sections such as disclosed in U.S. Pat. No. 5,785,649 or when the stay has a ball and link member such as disclosed in U.S. Pat. No. 3,762,401. The enlarged diameter sections prevent the elongated members from slipping through the blade notch 49.

The elongated member is held in place by the blade notch 49 or the flange notch 51 but may be easily removed at the end of a surgical procedure. The elongated member may be easily removed during a surgical procedure or adjusted or inserted into a different notch to adjust the tension of the stay.

The various parts of the surgical retractor system may be formed from materials including, but not limited to, injection molded plastic, stamped metal, casted metal or coated metal, to provide an inexpensive, sterile, disposable parts. Alternatively, reusable parts may be made from materials including, but not limited to, heat or radiation resistant plastics and stainless steel, that can be sterilized by conventional methods exemplified by autoclaving or gamma radiation treatment. The plastics include, but are not limited to, polycarbonate, polyphenylene ether and nylon. Optionally, the retractor frame 10 may be made of inexpensive, reusable die cast aluminum.

One method according to the present invention of retracting tissue at an incision during surgery includes the steps of: (a) applying a retractor frame conformed to fit a surface of a patient's body; (b) attaching a paddle arm to the frame, the arm having a blade assembly having a blade member for retracting tissue and having an extension having at least one notch adapted to receive a portion of a stay; (c) adjusting the arms to retract the tissue around the incision; and (d) removing the frame after completing the surgical procedure. The paddle arms and blade assembly may be attached to the frame before or after the frame is fitted to the patient's body. The method may optionally include the step (e) of attaching a surgical retractor stay having a hook member and an elongated member by engaging tissue with the hook member and inserting the elongated member in a notch on the frame or blade assembly. The method may optionally include the step (f) locking the paddle arms into position. The method may optionally include the step (f) of attaching a snap-on lighted surgical retractor to the frame. The method may also include the step (g) of sterilizing all or part of the surgical retractor system for reuse.

According to the invention, the improved surgical retractor system has paddle arms 18 and an elastic band 17 which aid in self-positioning of the frame 10. The frame 10 also includes apertures 12 and hubs 14 which cooperate to form a ratchet mechanism to reduce slippage of the paddle arms 18 during a surgical procedure. A cam lock pin 16 may engage indentations 40 in the aperture 12 to lock the paddle arms 18 into a fixed position to reduce accidental movement of the arms 18 during surgery.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed is:

1. A surgical retractor system for use in surgery comprising:
    a frame;
    a blade assembly having a blade member for retracting tissue and having an extension having a plurality of notches, wherein the notches are adapted to receive a portion of a surgical retractor stay; and
    a paddle arm having a first end and a second end, the second end connected to the blade member and the first end pivotally connected to the frame.

2. The system of claim 1, wherein the paddle arm is removably connected to the blade assembly.

3. The system of claim 1, wherein the paddle arm is formed as a unitary member with the blade assembly.

4. The system of claim 1 comprised of a material selected from the group consisting of aluminum, stainless steel, polycarbonate, polyphenylene ether and nylon.

5. A surgical retractor system for use in surgery comprising:
    a frame including an aperture having an edge with teeth;
    a hub having a bore; and
    a pin received by the bore and the aperture, wherein the pin couples the hub to the frame.

6. The system of claim 5, further comprising:
    a blade assembly; and
    a paddle arm having a first end connected to the hub and a second end connected to the blade assembly.

7. The system of claim 5 comprised of a material selected from the group consisting of aluminum, stainless steel, polycarbonate, polyphenylene ether and nylon.

8. The system of claim 5, wherein the frame is articulated.

9. The system of claim 8, wherein the frame comprises frame members hingedly connected to each other.

10. The system of claim 8, wherein the frame has a portion comprised of flexible metal or plastic.

11. The system of claim 5, wherein the hub further comprises a pinion.

12. A surgical retractor system for use in surgery comprising:
    a frame having an aperture;
    a hub having a bore;
    a pin received by the bore and the aperture, wherein the pin couples the hub to the frame, wherein the pin has a stud and the aperture has an indentation for receiving the stud and further wherein the stud and indentation cooperate to provide a cam locking mechanism.

13. A surgical retractor system for use in surgery comprising:
    a frame having an aperture;
    a hub having a bore;
    a pin received by the bore and the aperture, wherein the pin couples the hub to the frame;
    a blade assembly; and
    a paddle arm having a first end connected to the hub and a second end connected to the blade assembly, wherein the blade assembly further comprises an extension having notches for receiving a portion of a surgical retractor stay.

14. A surgical retractor system for use in surgery comprising:
    a frame having an aperture;
    a hub having a bore; and
    a pin received by the bore and the aperture, wherein the pin couples the hub to the frame,
    wherein the aperture includes a plurality of teeth and the hub includes a plurality of projections, the pluralities of teeth and projections cooperating to provide a ratchet mechanism.

15. A surgical retractor system for use in surgery comprising:
    a frame having an aperture and a plurality of notches adapted to receive a portion of a surgical retractor stay;
    a hub having a bore; and
    a pin received by the bore and the aperture, wherein the pin couples the hub to the frame.

16. The system of claim 15, wherein the flange is concave.

17. A surgical retractor system for use in surgery comprising:
a frame having a plurality of apertures,
a plurality of hubs, each hub having a bore and a pinion;
a pin received by one of the hub bores and one of the apertures, wherein the pin couples the hub to the frame; and
an elastic band adapted to cooperate with the pinions of two hubs.

18. A surgical retractor system for use in surgery comprising:
a frame having an aperture and a plurality of teeth;
a hub having a bore and a plurality of projections;
a pin received by the bore and the aperture, wherein the teeth and projections cooperate to provide a ratchet mechanism.

19. The system of claim 18, wherein the pin has a stud and the aperture has an indentation for receiving the stud and further wherein the stud and indentation cooperate to provide a cam locking mechanism.

20. The system of claim 18, further comprising:
a blade assembly; and
a paddle arm having a first end connected to the hub and a second end connected to the blade assembly.

21. The system of claim 20, wherein the blade assembly further comprises an extension having notches for receiving a portion of a surgical retractor stay.

22. The system of claim 18, wherein the frame further comprises a flange having a plurality of notches adapted to receive a portion of a surgical retractor stay.

23. The system of claim 18, wherein the flange is concave.

24. The system of claim 18 comprised of a material selected from the group consisting of aluminum, stainless steel, polycarbonate, polyphenylene ether and nylon.

25. The system of claim 18, wherein the frame is articulated.

26. The system of claim 25, wherein the frame comprises frame members hingedly connected to each other.

27. The system of claim 25, wherein the frame has a portion comprised of flexible metal or plastic.

28. The system of claim 18, wherein the hub further comprises a pinion.

29. The system of claim 28, further comprising an elastic band adapted to cooperate with the pinion of the hub and another pinion of a second hub.

30. A surgical retractor system for use in surgery comprising:
(a) a blade assembly having a blade member and an extension having a plurality of notches adapted to receive a portion of a surgical retractor stay;
(b) a frame having a plurality of apertures and a plurality of teeth substantially surrounding each aperture, each aperture including an indentation;
(c) a hub having a bore and a plurality of projections; and
(d) a pin having a stud, the pin received by the bore and one of the apertures, wherein the pin couples the hub and frame, and the teeth and the projections cooperate to provide a ratchet mechanism, and wherein the stud and indentation cooperate to provide a cam locking mechanism.

31. A method of retracting tissue at an incision during a surgical procedure using a retractor frame having an aperture, a hub having a bore, and a pin received by the bore and the aperture and coupling the hub to the frame, wherein the pin has a stud and the aperture has an indentation for receiving the stud and further wherein the stud and indentation cooperate to provide a cam locking mechanism, the method comprising the steps of:
(a) applying a retractor frame conformed to fit a surface of a patient's body;
(b) attaching a paddle arm to the frame, the paddle arm having a blade assembly having a blade member that includes an extension adapted to receive a portion of a stay;
(c) adjusting the paddle arm to retract the tissue; and
(d) removing the frame after completing the surgical procedure.

32. The method of claim 31, wherein the hub includes a pinion.

33. A method of retracting tissue at an incision during a surgical procedure using a retractor frame having an aperture and a hub, wherein the aperture includes a plurality of teeth and the hub includes a plurality of projections, the pluralities of teeth and projections cooperating to provide a ratchet mechanism, the method comprising the steps of:
(a) applying the retractor frame conformed to fit a surface of a patient's body;
(b) attaching a paddle arm to the retractor frame, the paddle arm having a blade assembly having a blade member that includes an extension adapted to receive a portion of a stay;
(c) adjusting the paddle arm to retract the tissue; and
(d) removing the retractor frame after completing the surgical procedure.

34. The method of claim 33, wherein the frame includes a second aperture and a second hub, each of the hubs including a pinion, further comprising the step of attaching an elastic band to the pinions of the hubs.

* * * * *